United States Patent [19]

Lapin et al.

[11] Patent Number: 4,749,807

[45] Date of Patent: Jun. 7, 1988

[54] VINYL ETHER TERMINATED ESTER OLIGOMERS

[75] Inventors: Stephen C. Lapin, Wauconda; Stephen A. Munk, Chicago, both of Ill.

[73] Assignee: Allied-Signal Inc., Morristown, N.J.

[21] Appl. No.: 15,256

[22] Filed: Feb. 17, 1987

[51] Int. Cl.[4] .................. C07C 69/80; C07C 69/34
[52] U.S. Cl. ...................... 560/91; 521/172; 521/176; 560/81; 560/198
[58] Field of Search ................ 560/81, 91, 198

[56] References Cited

U.S. PATENT DOCUMENTS

| | | | |
|---|---|---|---|
| 4,074,061 | 2/1978 | Musser | 560/198 X |
| 4,100,354 | 7/1978 | Owen | 560/91 X |
| 4,440,945 | 4/1984 | Conciatori et al. | 560/86 |

*Primary Examiner*—Werren B. Lone
*Assistant Examiner*—Vera C. Clarke
*Attorney, Agent, or Firm*—Thomas K. McBride; John F. Spears, Jr.; Eugene I. Snyder

[57] ABSTRACT

There are described vinyl ether terminated ester oligomers which cure or polymerize particularly rapidly, especially by cationic polymerization which is radiation induced in the presence of an onium salt. The oligomeric units arise most often from the reaction of a dicarboxylic acid with a diol, although esters with triols and higher polyhydric polyols also are useful, especially where an extensively cross-linked product is desired. The carboxyl-terminated oligomeric esters are esterified with vinyl ether terminated alcohols which can be thought of as the adducts of alkynes and polyols, especially diols.

35 Claims, No Drawings

VINYL ETHER TERMINATED ESTER OLIGOMERS

BACKGROUND OF THE INVENTION

Vinyl ethers are extremely reactive monomers which are known to undergo polymerization by a cationic mechanism and are useful in applications which require a high speed curing of a resin formulation. The vinyl ethers react much faster than the epoxy resins and therefore may be used for printing inks, coatings, elastomers, foams, and other types of materials dependent upon the ability of the resin to cure at a rate which is consistent with other processing steps. A disadvantage attendant to the use of vinyl ethers is that their commercial availability is relatively limited. In general, the available vinyl ethers are low molecular weight monofunctional or difunctional monomers, whereas in most commercial applications higher molecular weight oligomeric materials are preferred.

The present invention discloses vinyl ether terminated esters. As will be seen, the structure of such esters is susceptible to wide variations with a minimum change in the reactants. This flexibility permits facile variation in the properties and characteristics of the vinyl ether terminated ester oligomers as well as comparable variations in the resulting cured resins. Where the oligomer contains more than one vinyl ether group the cured resins are extensively cross-linked, very high molecular weight polymers. The polymers are thermosetting materials with a wide range of properties depending upon the structure of the oligomeric precursor. Although the vinyl ether terminated esters of this invention have been designed to fill the need for radiation curable coatings, they may have a much broader use. In particular, the esters of our invention are readily polymerized by means other than radiation curing, and the resulting polymers are meant to be subsumed in our invention.

SUMMARY OF THE INVENTION

The purpose of our invention is to provide vinyl ethers which are readily and economically synthesized and with structures whose permutations are large in number but each of which are easily made, with at least most of the resulting materials able to be radiation cured to afford polymer coatings. An embodiment is the vinyl ether terminated oligomeric esters. In a more specific embodiment the alcohol portion of the ester is a vinyl ether which can be viewed as the adduct of an acetylenic compound and an ethylene or propylene glycol. In another embodiment the alcohol portion of the ester is a vinyl ether which may be viewed as the adduct of an acetylenic compound and a poly(ethylene) or poly(propylene) glycol. In a further embodiment the acetylenic compound is a terminal acetylene. In a still further embodiment the acid portion of the ester is a dicarboxylic acid. In yet another specific embodiment a glycol is used as a chain extender for the oligomeric ester. Other embodiments will become apparent from the detailed discussion within.

DESCRIPTION OF THE INVENTION

The invention to be described in greater detail within is a class of compounds with a broad spectrum of molecular weight but which is characterized by the presence of one or more terminal vinyl ether moieties and which are esters of carboxylic acids. One of the reactants used in making the product of our invention is, or may be viewed as, an adduct of an acetylenic compound (an alkyne) with a polyol, the resulting material being a vinyl ether terminated alcohol. For simplicity, a generic alcohol, HOXOH, will be used in this section as respresentative of polyols generally in order to represent one means of preparing the vinyl ether terminated alcohol under discussion, namely,

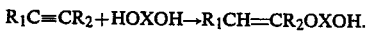

If the vinyl ether terminated alcohol is prepared as an adduct, usually reaction conditions are so chosen as to form the monoadduct either to the virtual exclusion of the diadduct or, more likely, in large preponderance relative to the diadduct. The monoadduct can be isolated and used in a purified form, but more often the entire reaction mixture is used as the alcoholic reactant in ester formation with carboxylic acids, where the unreacted glycol (or polyol) has the important function of a chain extender.

The vinyl ether terminated alcohol is then reacted with a carboxylic acid. In reality, the alcohol is reacted with some activated derivative of a carboxylic acid, such as an acid chloride or ester, but for simplicity and clarity of exposition we shall continue to refer to reaction with a carboxylic acid. In perhaps the most important case where the acid is a dicarboxylic acid the reaction may be represented as,

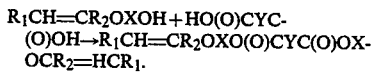

The above reaction is most accurate where the alcoholic reactant is solely

and in the more usual cases where the alcoholic reactant is a mixture containing unreacted glycol (or polyol), or where a second glycol (or polyol) is added to the vinyl ether terminated alcohol, the product can be envisioned as arising from the reaction sequence,

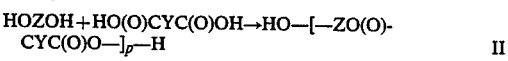

The oligomeric ester II can then react with the vinyl ether terminated monomeric ester I to afford the new ester III which can be end-capped by esterification with a vinyl ether terminated alcohol to afford the oligomeric product IV, as shown below

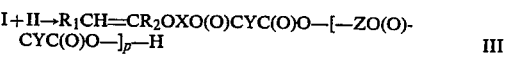

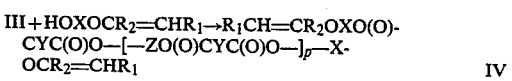

The oligomeric esters of structure IV need not arise from the precise reaction sequence shown above, for other sequences can lead to the same oligomeric esters. The foregoing sequence was illustrated for convenience in following the preparative route to our esters and in arriving at our structural representation of the oligomeric esters of our invention. The structure, IV, will be used in the subsequent description of our invention.

The vinyl ether terminated alcohols which are used in preparing the oligomeric esters of this invention have a structure corresponding to the adduct of an alkyne and a polyol. It must be emphasized that although some of the vinyl ether terminated alcohols of this invention may in fact be made by the addition of polyols to alkynes, the vinyl ether terminated alcohols herein also can be made in other ways, and the alternative routes to such alcohols are often preferred. The alkyne has the generic formula $R_1C \equiv CR_2$, and the polyol has the generic formula $X(OH)_s$, where s is an integer which is 2, 3, 4, .... The generic formula of the vinyl ether terminated alcohols of our invention is then $R_1CH=CR_2OX(OH)_{s-1}$.

The groupings $R_1$ and $R_2$ are independently selected from the group consisting of hydrogen and lower alkyl moieties containing from 1 to 10 carbon atoms, although those with from 1 to about 4 carbon atoms are favored. It is preferable that both $R_1$ and $R_2$ are not alkyl moieties, for in the case where both are lower alkyl groups this causes a reduction in polymerization rate of the oligomers of our invention to a point where the polymerization rate is undesirable. Where $R_1$ is an alkyl moiety it is preferred that $R_2$ be hydrogen, and conversely; those cases where $R_2$ is hydrogen and $R_1$ an alkyl of 1 to 4 carbons are quite desirable. In a preferred embodiment $R_1$ ($R_2$) is a methyl group and $R_2$ ($R_1$) is hydrogen. In a still more preferred embodiment both $R_1$ and $R_2$ are hydrogen.

In the vinyl ether alcohol fragment the grouping $-OX(OH)_{s-1}$ arises from, or can be thought of as arising from, a polyol of structure $X(OH)_s$, where s is an integer equal to or greater than 2. The most usual cases are those where s is 2, 3, or 4, with the most important case being that where s=2, that is, the polyol is a diol.

Among the diols HOXOH supplying the necessary grouping in the vinyl ether alcohol fragment one important class consists of alkylene glycols, $HO(C_nH_{2n})OH$, where n is an integer from 2 to about 10. The linear alkylene glycols, $HO(CH_2)_nOH$, (polymethylenediols), where n is an integer from 2 to about 10, are particularly useful, especially where n is from 2 to about 6. Illustrative of the members of this group are such diols as ethylene glycol, 1,3-propylene glycol, 1,4-butanediol, 1,5-pentanediol, 1,6-hexanediol, 1,7-heptanediol, 1,8-octanediol, 1,9-nonanediol, and 1,10-decanediol (decamethylene glycol).

The nonlinear or branched alkylene diols also may be used to supply the fragment —OXOH, where such glycols contain from 3 up to about 10 carbon atoms. Examples include 1,2-propylene glycol, 2,3-butanediol, 2,3-dimethyl-2,3-butanediol, 2,3-dimethyl-1,4-butanediol, etc.

Another class of diols useful as a source of the grouping —OXOH are the polyalkyleneoxy glycols, especially poly(ethyleneoxy) glycols, $[-CH_2CH_2O-]_m$, and poly(propyleneoxy) glycol, $[-CH(CH_3)C-H_2O-]_m$, where m is an integer from 1 up through about 50, although more usually m is an integer from 1 up to about 10, and most preferably from 1 up to about 5. Examples of the glycols in this branch of the invention include diethylene glycol, triethylene glycol, tetraethylene glycol, pentaethylene glycol, hexaethylene glycol, etc., along with the analogs of the propyleneoxy glycols.

Among the fragments whose parents are triols, $X(OH)_3$, may be mentioned trimethylolpropane, glycerol, trishydroxyethyl trimethylolpropane, and pentaerythritol monomethyl ether. Among the fragments whose parent is a tetrahydroxy compound, $X(OH)_4$, may be mentioned such polyols as pentaerythritol and tetrahydroxyethyl pentaerythritol.

The vinyl ether terminated alcohol is then reacted with a carboxylic acid, generally a polycarboxylic acid, to afford a vinyl ether terminated ester. There are four quite distinct variants here. In one variant the purified vinyl ether terminated alcohol alone is reacted with the acid. In a second variant a mixture of the vinyl ether terminated alcohol and the unreacted polyol from which it was made, or could be thought of as being made, is reacted with the acid. In this variant the polyol acts as a chain extender by esterifying the polycarboxylic acid to give an oligomeric ester where X=Z. In another variant a mixture of the vinyl ether terminated alcohol and a second, unrelated polyol is reacted with the acid. Again the polyol acts as a chain extender via ester formation with the carboxylic acid, but in this case X and Z are different. Finally, in a fourth variant a mixture of vinyl ether terminated alcohol, unreacted polyol from which it was made or could be thought to be made, and a second, unrelated polyol is reacted with the carboxylic acid. As in the cases above, the unreacted polyols react with the carboxylic acid to afford oligomeric esters, and in this variant some of Z are different from X and some are the same.

The components of the alcohol mixture reacting with the carboxylic acid are $R_1CH=CR_2OX(OH)_{s-1}$ (component A), $X(OH)_s$ (component B), and $Z(OH)_s$ (component C), where $Z(OH)_s$ is from the same group as $X(OH)_s$, but merely denotes a different member of that group. In the reactant alcohol mixture the molar proportions of (B+C)/A may be between 0 and about 100. Where the ratio is 0 there is no free polyol. This is the unusual and exceptional case; generally the alcohol mixture will contain not only a vinyl ether terminated alcohol but also some polyol. In the preferred case the ratio above is between about 0.5 and about 10.

As alluded to above, the reaction between alcohols and carboxylic acids to give the esters of this invention is too slow to be a practical method of preparation, and activated derivatives of carboxylic acids are in fact used as reactants. Among such derivatives the acid chlorides and esters are most frequently employed, and the following description refers to the carboxylic acids which are parents of the activated acid derivatives used to prepare our oligomeric esters.

Turning to the carboxylic acids which may be used, or which are parents of activated derivatives which may be used in the practice of this invention, it has previously been mentioned that polycarboxylic acids are generally favored. However, useful products are obtained from monocarboxylic acids. In this case the alcohol mixture contains the vinyl ether terminated alcohol with little, if any, unreacted polyols. The product is an ester which may be represented as,

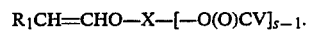
$R_1CH=CHO-X-[-O(O)CV]_{s-1}$.

It can be seen that this is a relatively low molecular weight material and is the least important of the class of esters which we have discovered. This class of esters is used as an additive to make cured polymers more flexible, especially where the cured polymers are extensively cross-linked. The product structure as given also is meant to indicate that few, if any, unreacted alcoholic hydroxyl groups remain in the product.

The moiety V may be an alkyl group, especially those containing up to about 20 carbon atoms, a cycloalkyl group, an aryl, alkaryl or aralkyl group. Examples of the alkyl moieties which may be used for V include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, and eicosyl. Examples of aryl groups include phenyl, naphthyl, anthryl, phenanthryl, etc. Cycloalkyl groups include the cyclopentyl, cyclohexyl, cycloheptyl, cyclooctyl, and cycloalkyl groups containing 1 or more alkyl side chains on the nucleus. Similarly, the aryl groups which may be used for V also may contain one or more alkyl groups on the aromatic ring, especially where such alkyl groups contain up to about 6 carbon atoms. Finally, examples of aralkyl groups include benzyl, 1-phenethyl, 2-phenethyl, 3-phenylpropyl, 2-phenylpropyl, 1-phenylpropyl, etc.

Perhaps the most important case is that where the carboxylic acid is a dicarboxylic acid which is esterified with an alcohol mixture of a vinyl ether terminated alcohol having appreciable amounts of unreacted polyol. The dicarboxylic acids which are most useful in this branch of the invention are those which are typically used in polyamide (nylon) and polyester fiber production, and include aromatic dicarboxylic acids such as the phthalic acids, especially isophthalic and terephthalic acid. The polymethylene dicarboxylic acid series also is important and is exemplified by the formula $HO_2C(CH_2)_rCO_2H$, where r is an integer from 2 up to about 10. The examples of this series include succinic, glutaric, adipic, pimelic, suberic, azelaic, and sebacic acids, with adipic acid being the outstanding member of this case. Other dicarboxylic acids which may be used in the practice of this invention include para-phenylene diacetic acid, paraphenylene dipropionic acid, 4,4'-dibenzylic acid, 5-t-butylisophthalic acid, and 1,6-naphthalene dicarboxylic acid.

Where the alcohol mixture contains 1 or more diols there are 3 subvariants possible. In all cases the alcohol mixture contains at least one vinyl ether terminated alcohol, and the subvariants are the cases where the mixture also contains the diol containing the structural grouping found in the ether, an unrelated diol, or a mixture of the above. In either of these cases, the ratio of molar proportions of diol to vinyl ether terminated alcohol is from about ½ to about 100, preferably from about ½ to about 10. Therefore, in the formula IV p equals 1–200, but preferably from 1–20.

In still a third case the polycarboxylic acid is a dicarboxylic acid but the alcohol mixture used to esterify the acid contains either a vinyl ether terminated alcohol containing a structural grouping arising from at least a trihydric polyol or, more likely, contains at least a trihydric polyol in the reaction mixture, or both. The structure of the resulting product is capable of enormous permutation. For example, each of the hydroxyls of the polyol can react with a different oligomeric ester subunit arising from the reaction of a dicarboxylic acid and a polyol. Also, in any subunit of the oligomer ester a polyol may react with various carboxyl groups to afford extensively cross-linked subunits. An important characteristic of this branch of the reaction is that in all cases there are essentially no free hydroxyl groups arising from the polyol in the final product. That is, less than about 5% of the initial hydroxyl groups of the polyols remain unreacted. This is desirable to afford a polymer with good characteristics. The descriptions and limitations previously mentioned are otherwise applicable, and in particular the molar proportion of polyol to vinyl ether terminated alcohol is between about 0.5 and about 100.

The vinyl ether terminated oligomeric esters of this invention may be cured or polymerized by any method known in the art. For example, the resins may be radiation cured, as for example by being subjected to an electron beam of an energy in the range from about 50 up to perhaps 500 KeV with a dosage from about 0.1 to about 10.0 Mrads. Electron beam curing may be performed advantageously in the presence of an iodonium or a sulfonium salt to afford high speed cationic polymerization. Ultraviolet curing in the presence of an onium salt also may be executed to afford cationic polymerization. Other means include thermal curing in the presence of a Lewis acid, such as boron trifluoride, or in the presence of a strong acid such as p-toluenesulfonic acid and trifluoromethylsulfonic acid. All these methods of polymerization are well known to those versed in the art and need not be elaborated upon further.

The following examples are only illustrative of our invention which is not to be limited thereto or circumscribed thereby in any way.

EXAMPLE I

To form a hydroxy vinyl ether, 250 mL of triethylene glycol and 7.5 grams of ground potassium hydroxide as catalyst were added to a 500 mL round bottom flask equipped with a mechanical stirrer, reflux condenser, and gas inlet tube. The mixture was heated to a temperature of about 190° C. while being purged with nitrogen. After the temperature was stabilized, a flow of acetylene at a rate of about 1.0 liters/minute was initiated, and the reaction was allowed to continue for a period of 5 hours. The flask was then fitted with a distillation head and 125 mL of reaction product was collected in a boiling range of 70° to 84° C. at 0.3 torr. Gas chromatographic analysis disclosed that the product was a mixture of 14% triethylene glycol divinyl ether, 78% triethylene glycol monovinyl ether, and 7% unreacted triethylene glycol. Redistillation of the product resulted in 85 mL of a fraction which contained 95% triethylene glycol monovinyl ether.

A solution of terephthaloyl chloride (2.88 g, 0.014 mol) in 25 mL of methylene chloride was added dropwise at room temperature to a mixture of triethylene glycol monovinyl ether (5.0 g, 0.028 mol), triethylamine (6 mL), 4-dimethylaminopyridine (DMAP) (0.05 g) and methylene chloride (40 mL). The mixture was stirred for 20 min. after the addition was complete and then it was washed two times with 100 mL of each of the following aqueous solutions: 2% phosphoric acid, 5% NaHCO$_3$, 5% NaCl. After the remaining solvent was removed at reduced pressure a clear thick liquid product remained (84% yield). The IR and proton NMR spectra were consistent with the expected product;

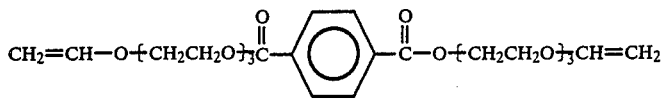

EXAMPLE 2

In this example a polyol was added as a chain extender. Thus, triethylene glycol monovinyl ether, terephthaloyl choride, and triethylene glycol were reacted in a 2:2:1 mole ratio under the conditions given in Example 1. GPC analysis showed a mixture of products with an average molecular weight of 690.

EXAMPLE 3

Triethylene glycol monovinyl ether (TEGMVE) and dimethyl terephthalate were combined in a 4:1 mole ratio in the presence of 0.5% titanium tetraisopropoxide. The mixture was heated at 180°±10° C. under a nitrogen atmosphere until approximately 80% of the theoretical yield of methanol was distilled from the mixture. The mixture was cooled and then placed under reduced pressure (0.2 to 5.0 torr). The temperature was slowly increased to remove the remaining methanol and to distill off the excess TEGMVE. The product was a clear thick liquid. The IR and $^1$HNMR spectra were consistent with the expected product;

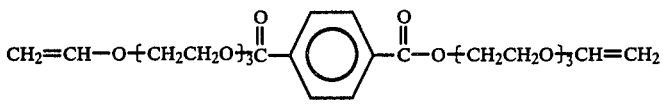

EXAMPLE 4

The procedure in Example 3 was repeated except that butanediol monovinyl ether was used in place of TEGMVE. The product is a low melting waxy solid. The IR and $^1$HNMR spectra were consistent with the expected product.

EXAMPLE 5

The procedure in Example 4 was repeated except that dimethylisophthalate was used in place of dimethylterephthalate. The product was a clear thick liquid.

EXAMPLE 6

The procedure in Example 5 was repeated except that 0.5 equivalents of butanediol were added as a chain extender. The resulting product was a low melting waxy solid.

EXAMPLE 7

The procedure in Example 5 was repeated except that 0.25 equivalents of trimethylol propane were included in the reaction mixture to increase the molecular weight and to increase the functionality of the product. The product was a waxy solid.

EXAMPLE 8

A triaryl sulfonium salt (UVE-1016, General Electric) was added (3%) to the materials described in Examples 3 to 7 above. The mixtures were coated onto a polyethylene substrate and were irradiated by a 160 KeV electron beam. All of the mixtures gave tack-free clear, colorless coatings with an energy dosage of less than 3.0 Mrads.

What is claimed is:

1. A vinyl ether terminated oligomeric ester of the formula, $$R_1CH=CR_2OXO(O)CYC(O)O-[-ZO(O)CYC(O)O-]_p-XOCR_2=CHR_1$$

where: $R_1$ and $R_2$ are independently selected from the group consisting of hydrogen and lower alkyl moieties containing up to about 10 carbon atoms;

X and Z are independently selected from a group such that
  (a) HOXOH and HOZOH are alkylene diols of the formula $HO(C_nH_{2n})OH$, where n is an integer from 2 to about 10; or
  (b) HOXOH and HOZOH are poly(ethyleneoxy) or poly(propyleneoxy) glycols, $HO-[-CH_2CH_2O-]_m-H$ or $HO-[-CH(CH_3)CH_2-]_m-H$, respectively, where m in an integer from 1 to about 50; or
  (c) $X(OH)_s$ and $Z(OH)_s$ are higher polyols, where s is an integer which is at least 3;

p is 0 or an integer from 1 to about 200; and
$HO_2CYCO_2H$ is a dicarboxylic acid selected from the group consisting of phthalic acids, polymethylene dicarboxylic acids, $HO_2C(CH_2)_rCO_2H$, where r is an integer from 2 to about 8, para-phenylene diacetic acid, paraphenylene dipropionic acid, 5-t-butylisophthalic acid and 4,4'-dibenzylic acid.

2. The vinyl ether terminated oligomer of claim 1 where $R_2$ is hydrogen and $R_1$ is an alkyl group of 1 to about 4 carbon atoms.

3. The vinyl ether terminated oligomer of claim 1 where $R_1$ and $R_2$ are hydrogen.

4. The vinyl ether terminated oligomer of claim 1 where $R_1$ is hydrogen and $R_2$ is methyl, or $R_1$ is methyl and $R_2$ is hydrogen.

5. The vinyl ether terminated oligomer of claim 1 where X is the same as Z.

6. The vinyl ether terminated oligomer of claim 1 where HOXOH and HOZOH are linear polymethylenediols, $HO(CH_2)_nOH$, where n is an integer from 2 to about 10.

7. The vinyl ether terminated oligomer of claim 5 where the polymethylenediols have from 2 to about 6 carbon atoms.

8. The vinyl ether terminated oligomer of claim 1 where HOXOH and HOZOH are poly(ethyleneoxy) or poly(propyleneoxy) glycols where m is an integer from 1 through about 10.

9. The vinyl ether terminated oligomer of claim 8 where m is an integer from 1 to about 5.

10. The vinyl ether terminated oligomer of claim 1 where p is an integer from 1 to about 20.

11. The vinyl ether terminated oligomer of claim 1 where $HO_2CYCO_2H$ is a phthalic acid.

12. The vinyl ether terminated oligomer of claim 11 where the acid is terephthalic acid.

13. The vinyl ether terminated oligomer of claim 11 where the acid is isophthalic acid.

14. The vinyl ether terminated oligomer of claim 1 where $HO_2CYCO_2H$ is adipic acid.

15. A vinyl ether terminated oligomeric ester containing fewer than 5% unreacted alcoholic hydroxyl groups which is the reaction product of a mixture of alcohols containing 1 molar proportion of a vinyl ether terminated alcohol of the formula,

$$R_1CH{=}CR_2OX(OH)_{s-1},$$

and from 0.5 to about 100 molar proportions of a polyol of formula $Z(OH)_t$ with a sufficient amount of a dicarboxylic acid such that there are essentially no free alcoholic hydroxyl groups in the resulting ester, where: $R_1$ and $R_2$ are independently selected from the group consisting of hydrogen and lower alkyl moieties containing up to about 10 carbon atoms;

X is independently selected from a group such that
(a) HOXOH is an alkylene diol of the formula $HO(C_nH_{2n})OH$, where n is an integer from 2 to about 10; or
(b) HOXOH is a poly(ethyleneoxy) or poly(propyleneoxy) glycol, $HO{-}[{-}CH_2CH_2O{-}]_m{-}H$ or $HO{-}[{-}CH(CH_3)CH_2{-}]_m{-}H$, respectively, where m is an integer from 1 to about 50; or
(c) $X(OH)_s$ is a higher polyol, where s is an integer which is at least 3; and $Z(OH)_t$ is a polyol where t is an integer which is at least 3.

16. The vinyl ether terminated oligomer of claim 15 where $R_2$ is hydrogen and $R_1$ is an alkyl group of 1 to about 4 carbon atoms.

17. The vinyl ether terminated oligomer of claim 15 where $R_1$ and $R_2$ are hydrogen.

18. The vinyl ether terminated oligomer of claim 15 where $R_1$ is hydrogen and $R_2$ is methyl, or $R_1$ is methyl and $R_2$ is hydrogen.

19. The vinyl ether terminated oligomer of claim 1 where HOXOH is a linear polymethylenediol, $HO(CH_2)_nOH$, where n is an integer from 2 to about 10.

20. The vinyl ether terminated oligomer of claim 19 where the polymethylenediol has from 2 to about 6 carbon atoms.

21. The vinyl ether terminated oligomer of claim 15 where HOXOH is a poly(ethyleneoxy) or poly(propyleneoxy) glycol where m is an integer from 1 through about 10.

22. The vinyl ether terminated oligomer of claim 21 where m is an integer from 1 to about 5.

23. The vinyl ether terminated oligomer of claim 15 where the dicarboxylic acid is selected from the group consisting of phthalic acids, polymethylene dicarboxylic acids, $HO_2C(CH_2)_rCO_2H$, where r is an integer from 2 to about 8, para-phenylene diacetic acid, para-phenylene dipropionic acid, 5-t-butylisophthalic acid and 4,4'-dibenzylic acid.

24. The vinyl ether terminated oligomer of claim 15 where the dicarboxylic acid is a phthalic acid.

25. The vinyl ether terminated oligomer of claim 24 where the acid is terephthalic acid.

26. The vinyl ether terminated oligomer of claim 24 where the acid is isophthalic acid.

27. The vinyl ether terminated oligomer of claim 15 where the acid is adipic acid.

28. A vinyl ether terminated ester of the formula,

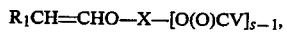

$$R_1CH{=}CHO{-}X{-}[O(O)CV]_{s-1},$$

where: $R_1$ and $R_2$ are independently selected from the group consisting of hydrogen and lower alkyl moieties containing up to about 10 carbon atoms;

s is an integer which is at least 2;

X is independently selected from a group such that
(a) HOXOH is an alkylene diol of the formula $HO(C_nH_{2n})OH$, where n is an integer from 2 to about 10; or
(b) HOXOH is a poly(ethyleneoxy) or poly(propyleneoxy) glycol, $HO{-}[{-}CH_2CH_2O{-}]_m{-}H$ or $HO{-}[{-}CH(CH_3)CH_2{-}]_m{-}H$, respectively, where m in an integer from 1 to about 50; or
(c) $X(OH)_s$ is a higher polyol, where s is an integer which is at least 3; and V is selected from the group consisting of alkyl containing up to about 20 carbons, a cycloalkyl, aryl, or aralkyl moiety.

29. The vinyl ether terminated ester of claim 28 where $R_2$ is hydrogen and $R_1$ is an alkyl group of 1 to about 4 carbon atoms.

30. The vinyl ether terminated ester of claim 28 where $R_1$ and $R_2$ are hydrogen.

31. The vinyl ether terminated ester of claim 28 where $R_1$ is hydrogen and $R_2$ is methyl, or $R_1$ is methyl and $R_2$ is hydrogen.

32. The vinyl ether terminated ester of claim 28 where HOXOH is a linear polymethylenediol, $HO(CH_2)_nOH$, where n is an integer from 2 to about 10.

33. The vinyl ether terminated ester of claim 32 where the polymethylenediols have from 2 to about 6 carbon atoms.

34. The vinyl ether terminated ester of claim 28 where HOXOH is a poly(ethyleneoxy) or poly(propyleneoxy) glycol where m is an integer from 1 through about 10.

35. The vinyl ether terminated ester of claim 34 where m is an integer from 1 to about 5.

* * * * *